United States Patent [19]

Morris

[11] 4,158,668

[45] Jun. 19, 1979

[54] PREPARATION OF CARBOXYLIC ACIDS FROM INTERNAL OLEFINS

[75] Inventor: Donald E. Morris, Kirkwood, Mo.

[73] Assignee: Monsanto Company, St. Louis, Mo.

[21] Appl. No.: 841,424

[22] Filed: Oct. 12, 1977

[51] Int. Cl.$^2$ .......................... C11C 1/00; C07C 51/00
[52] U.S. Cl. ...................................... 260/413; 562/522
[58] Field of Search ....... 260/413 HC, 533 A, 514 M; 562/522

[56] References Cited

U.S. PATENT DOCUMENTS

| 2,448,368 | 8/1948 | Gresham et al. | 260/514 M |
| 3,661,957 | 5/1972 | Shubkin | 260/413 HC |
| 3,980,683 | 9/1976 | Isa et al. | 260/413 HC |

Primary Examiner—John Niebling
Attorney, Agent, or Firm—S. M. Tarter; E. P. Grattan; F. D. Shearin

[57] ABSTRACT

The present process is suitable for preparing carboxylic acids wherein greater than 50 mole percent of the carboxylate groups are at the terminal position which comprises bringing together in a reaction zone an olefin or mixture of olefins wherein greater than 50 mole percent of the olefin has unsaturation at other than the terminal position, water and carbon monoxide in the presence of a cobalt catalyst and a pyridine-type promoter, preferably pyridine, in a mole ratio of promoter to catalyst between about 5:1 and 15:1, at pressures from about 70 kilograms per square centimeter to about 300 kilograms per square centimeter, at temperatures between about 180° C. and about 220° C.

14 Claims, No Drawings

PREPARATION OF CARBOXYLIC ACIDS FROM INTERNAL OLEFINS

BACKGROUND OF THE INVENTION

This invention relates to a process for preparing carboxylic acids from olefins in the presence of a catalyst and more particularly relates to a process for preparing carboxylic acids wherein greater than 50 mole percent of the carboxylate groups are at the terminal position from an olefin wherein greater than 50 mole percent of the olefin has unsaturation at other than the terminal position.

Natural fatty acids, wherein the carboxylate group is virtually always at the terminal position of the alkyl chain, are widely used in industry for a variety of applications. The lower molecular weight fatty acids, such as those containing 6 to 10 carbon atoms, are used as intermediates to form plasticizers, surfactants or lubricants and in many other important uses in today's society. The higher molecular weight fatty acids, such as those containing an average of about 12 carbon atoms, are widely used in the preparation of toilet bar soaps. Millions of pounds of these natural fatty acids are consumed in the United States each year.

There is a need, however, to supplement the source of supply of these natural fatty acids and accordingly synthetic fatty acids produced from olefins are being used to supplement or even replace the natural products. However, in order to use synthetic fatty acids, in many applications it is necessary that the synthetic fatty acid have the carboxylate group at the terminal carbon atom.

The preparation of synthetic fatty acids by the reaction of olefins, carbon monoxide and water using a number of catalysts, such as a cobalt catalyst, is well known. As an example, U.S. Pat. No. 3,661,957 and U.S. Pat. No. 3,678,083 disclose processes for preparing carboxylic acids from higher olefins, say those having 10 or more carbon atoms in the olefin chain, carbon monoxide and water using a cobalt catalyst and a pyridine promoter. The prior art also discloses that the linearity of the acid product decreases with increasing temperature (see for example, P. Pino et al "Isomer Distribution in Products of Olefin Hydroformylation and Other Carbonylation Reactions", *La Chimica e L'Industria*, Vol. 50, No. 1, January 1968, pages 106–118).

Although satisfactory results are obtained using these and other processes in the prior art, the prior art processes fail to achieve the advantages of the present invention in one or more respects. Although temperatures of up to 180° C., preferably in the range of 140° to 160° C., are used with pyridine-type promoters and a cobalt catalyst, prior art processes teach that in order to obtain a carboxylic acid wherein most of the carboxylate groups are at the terminal position, it is necessary to use a feed of mostly alpha-olefin, which can be obtained only through special processing and is generally more expensive.

Now, according to the present invention, a process for preparing carboxylic acids wherein greater than 50 mole percent of the carboxylate groups are at the terminal position has been developed using an olefin feed that can contain as little as 10 percent or less of alpha-olefin by reaction at higher temperatures, all of which is contrary to the teachings of the prior art. Since the alpha-olefins are far more expensive as a feed material to the carboxylation process using carbon monoxide and water, those skilled in the art will recognize that there is a clear advantage to the process of the present invention.

SUMMARY OF THE INVENTION

These and other advantages are achieved by a process for preparing carboxylic acids which comprises bringing together in a reaction zone an olefin wherein greater than 50 mole percent of the olefin has unsaturation at other than the terminal position, water and carbon monoxide in the presence of a cobalt catalyst and a promoter selected from the group consisting of pyridine, isoquinoline, and alkyl pyridines having 1 to 4 carbon atoms in the alkyl chain, the mole ratio of promoter to catalyst being between about 5:1 and 15:1, at pressures from about 70 kilograms per square centimeter to about 300 kilograms per square centimeter, at temperatures above 180° C. and below about 220° C.

For the purposes of this invention, the term "olefin" shall mean any organic compound having at least one non-aromatic carbon-to-carbon double bond, and includes mono-olefins, polyolefins, cyclic compounds, branched and linear compounds. The term "internal olefin" as it is used in the specification and claims shall mean an olefin wherein the carbon-to-carbon double bond is other than at the terminal position, i.e., an isomer to an alpha-olefin. The term "linear acid" shall mean a carboxylic acid wherein the carboxylate group is at the end of the molecule, and the term "branched acid" shall mean a carboxylic acid wherein the carboxylate group is at a position other than the end of the molecule.

Any number of olefins containing greater than 50 mole percent internal olefin are useful feeds in the process of the present invention. Such olefins may also contain other functional groups such as halide, carboxy, carbonyl, hydroxy and the like, provided that these functional groups do not adversely affect the process of the present invention.

Although olefin feeds containing from 4 to 9 carbon atoms, such as butene, hexene, heptene, octene and the like, are useful in the process of the present invention, the greatest advantages are observed when the olefin feeds contain about 10 or more carbon atoms. Examples of useful olefins containing 10 or more carbon atoms include: pentadecene, ethyldodecene, undecene, dodecene, octadecene, 2-butyloctene, cyclododecene, dimethyldodecene, and the like. Mixtures of such olefins are also useful in the present invention.

Commercial mixtures of olefins can also be used as feeds in the present process. These commercial olefin mixtures are generally a mixture of various homologous olefins such as $C_{10}$, $C_{12}$, $C_{14}$ olefins; $C_{10}$, $C_{11}$ olefins; $C_{10}$, $C_{11}$, $C_{12}$ olefins; $C_{12}$, $C_{14}$, $C_{16}$ olefins; $C_{12}$, $C_{14}$ olefins; $C_{13}$, $C_{15}$, $C_{17}$ olefins; $C_{12}$, $C_{13}$, $C_{14}$, $C_{15}$, $C_{16}$ olefins; and higher olefin mixtures and the like. These commercial mixtures are synthesized for example by Ziegler catalyst polymerization of low molecular weight olefins such as ethylene or propylene; by dehydrogenation of suitable paraffins and the like. These commercial olefin mixtures can contain branched as well as straight-chain olefins. The mixed olefins thus obtained might also contain minor amounts of $C_6$–$C_8$ olefins, non-homologous olefins as well as non-olefin components. Such non-olefin components might be paraffins, alkyl halides, alcohols and the like; the nature of the non-olefin components is to a great degree dependent on the synthesis route utilized. The mixed olefins obtained from such a commercial synthesis need not be separated into the individual components to be useful. Mixtures containing from $C_{10}$ to $C_{20}$ internal olefins are preferred and such mixtures in the $C_{10}$ to $C_{14}$ olefin range are especially preferred.

The amount of alpha-olefin in the olefin feed is not important in the process of the present invention, but it is important to note that the olefinic linkage in commercial mixtures of olefins, such as those described in the preceding paragraph, is randomly distributed along the alkyl chain. At room temperature an equilibrium mixture of an olefin containing 10 to 14 carbon atoms will contain about 97 percent internal olefin and about 3 percent alpha-olefin. Although olefins can be prepared having a higher percentage of alpha-olefin by techniques known to those skilled in the art, high percentages of alpha-olefins are not necessary in the process of the present invention, although their presence is not harmful. A fatty acid product containing greater than 50 mole percent linear acid is obtained from olefins containing greater than 50 percent internal olefins, say as high as 75 or even greater than 90 percent.

As will occur to those skilled in the art, the present process can be carried out in the presence or absence of additional solvents known to the art. Typical solvents are the alkyl ketones having up to about 11 carbon atoms such as diisobutyl ketone, cyclohexanone, methylethyl ketone, and the like; and alkyl ethers having from 4 to about 16 carbon atoms such as diethyl ether, 1,4-dioxane, di-n-butyl ether, di-n-hexyl ether, diisopropyl ether and the like; and polyethers such as 1,2-diethoxy ethane, and the like. It is preferred to carry out the process in the presence of saturated carboxylic acids having 2 to 20 carbon atoms, such as acetic acid, decanoic acid, steric acid and the like, and especially preferred to use carboxylic acids of the same type being produced by the reaction, say acids having from 10 to 14 carbon atoms. Mixtures of these solvents can also be used.

The amount of solvent can range between about 10 percent and about 70 percent and usually is that amount of solvent required to form a solution at room temperature of the olefin and water reactants. As will occur to those skilled in the art, more or less solvent can be used and it is preferred in the process of the present invention to conduct the process in the substantial absence of solvents of the ketone and ether-type, but in the presence of carboxylic acids.

The catalysts which are used in the present process are cobalt-containing systems. The effective catalyst is thought to be a hydrido carbonyl complex; and thus any cobalt-containing compound, cobalt metal and the like which can yield such a complex under the reaction conditions can be used in the present process. Cobalt salts, e.g., cobalt hexanoate, cobalt chelates or cobalt complexes can be used to provide the catalyst, and dicobalt octacarbonyl is quite conveniently used. The amount of catalyst which can be employed is generally from about 0.001 to about 1.0 mole of cobalt per mole of olefin, and it is preferred to use about 0.1 mole of cobalt per mole of olefin.

The amount of water to be used in the present process can vary within wide limits. Ordinarily, at least one mole of water per double bond in the olefin is provided. Using a monoolefin for illustration purposes, the molar ratio of olefin to water can range from 1:1 to 1:6 or even higher. Olefin-water molar ratios ranging from 1:1 to about 1:3 are preferred.

The process of the present invention is generally carried out at elevated temperatures and pressures. The pressure is primarily due to the carbon monoxide reactant. Thus, pressures ranging from about 70 kilograms per square centimeter ($kg/cm^2$) to about 300 $kg/cm^2$ can be used and it is preferred to use a reaction pressure of about 200 $kg/cm^2$. The temperature can vary from about 180° C. to about 220° C. or higher. However, the yield of fatty acid product decreases rapidly at temperatures above about 200° C., and at temperatures below 180° C., the amount of linear acid in the fatty acid product decreases rapidly; hence, it is preferred to conduct the process of the present invention at temperatures above 180° C. and below about 200° C., say about 185° C., to obtain the optimum combination of higher reaction rates, yield, and higher amounts of linear acid.

The promoters which can be used in the process of the present invention are those known to those skilled in the art, and include pyridine, isoquinoline, and alkyl pyridines having 1 to 4 carbon atoms in the alkyl chain. Suitable alkyl pyridines include: beta and gamma picoline, the lutidines, 2-methyl-5-ethylpyridine, alpha-bromopyridine, 4-chloropyridine, 3-nitropyridine, and the like. Pyridine is preferred.

The concentration of promoter is conveniently based on the amount of cobalt present as the cobalt catalyst. Expressed in terms of molar ratio of promoter to cobalt in the cobalt catalyst, useful promoter ratios vary between 5:1 and 15:1. Ratios of promoter to cobalt higher than 15:1 tend to increase the amount of by-products at the expense of acid yield while ratios below about 5:1 do not significantly improve the linearity of the acid product. Ratios of promoter to cobalt between 10:1 and 15:1 provide good results and ratios between about 8:1 and about 12:1, say about 10:1, are preferred.

The fatty acid product obtained in the present carboxylation process is a mixture of linear acids and branched acids. This can be illustrated by the following general equation using an internal olefin, wherein $R_1$ and $R_2$ are individually an alkyl chain containing from 1 to 19 carbon atoms and the sum of the carbon atoms in $R_1$ and $R_2$ is between 2 and 20, $R_3$ and $R_4$ each is an alkyl chain having carbon atoms equal to the sum of the carbon atoms in $R_1$ and $R_2$.

$$R_1-CH=CH-R_2 + HOH + CO \xrightarrow{\text{catalyst}}$$

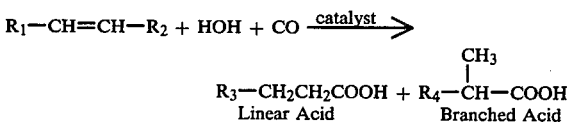

$$R_3-CH_2CH_2COOH + R_4-\underset{|}{\overset{CH_3}{C}}H-COOH$$
Linear Acid      Branched Acid

DESCRIPTION OF THE PREFERRED EMBODIMENTS

This invention is illustrated by but not limited to the following Examples.

EXAMPLES I-X

These Examples illustrate the process of the present invention by comparing the conversion of isomerized dodecenes containing about 90 percent alpha-olefin to dodecenes containing greater than 90 percent internal olefin. The data show the effect of temperature on the carboxylic acid linearity from the hydrocarboxylation of dodecenes.

To a stirred autoclave was charged 6.16 grams cobalt octacarbonyl (36 mmoles Co), 28.5 grams (360 mmoles)

pyridine, 45.7 grams (272 mmoles) dodecene and 31 milliliters of nonanoic acid as the solvent. The autoclave was pressurized to 200 kg/cm² with carbon monoxide and 1 percent by weight water was maintained in the autoclave by continuously pumping the water into the reaction zone. After two hours, the autoclave was depressurized and opened, and the reaction mass was analyzed by gas chromatography. The results are presented in the following tabulation:

| EXAMPLE | ALPHA-OLEFIN (mole %) | TEMPERATURE (°C.) | OLEFIN CONVERSION (mole %) | LINEAR ACID[a] (mole %) |
|---|---|---|---|---|
| I | 90 | 150 | 84 | 77 |
| II | 90 | 165 | 84 | 77 |
| III | 90 | 180 | 80 | 74 |
| IV | 90 | 190 | 80 | 76 |
| V | 90 | 200 | 78 | 74 |
| VI | 10.8 | 150 | 61 | 39 |
| VII | 10.8 | 165 | 76 | 58 |
| VIII | 10.8 | 180 | 86 | 65 |
| IX | 10.8 | 190 | 81 | 70 |
| X | 10.8 | 200 | 78 | 71 |

[a] amount of linear $C_{13}$ acid in total $C_{13}$ acid.

Thus, it can be seen that when an olefin feed containing a high percentage of alpha-olefin is converted to a fatty acid product, the amount of linear acid remains constant, or decreases somewhat, at increasing temperatures between 150° C. and 200° C. On the other hand, when an olefin feed containing a high percentage of internal olefin is converted to a fatty acid product, the amount of linear acid increases with increasing temperature to about the same amount at 200° C.

EXAMPLE XI

The general procedure of Examples I-X was followed except that a commercial mixture of equal portions of $C_{10}$, $C_{11}$ and $C_{12}$ olefins each containing greater than 90 mole percent internal olefins was used instead of the dodecene at a temperature of about 190° C. Analysis of the fatty acid product showed that there was an 80 percent conversion to equal ratios of $C_{11}$, $C_{12}$ and $C_{13}$ fatty acids, and the amount of linear acid in total acid was 65 mole percent.

EXAMPLE XII

The procedure of Example XI was repeated except that the ratio of pyridine to cobalt was about 5:1. The conversion of olefin to fatty acid was 57 percent, and the amount of linear acid in total acid was 72 mole percent.

EXAMPLE XIII

The procedure of Example XI was repeated except that the ratio of pyridine to cobalt was about 12:1. The conversion of olefin to fatty acid was 74 percent, and the amount of linear acid in total acid was 65 mole percent.

EXAMPLE XIV

The general procedure of Examples I-X was repeated except that the temperature and pressure were raised to 220° C., 280 kg/cm² respectively. The conversion of olefin to fatty acid was 85 percent, and the amount of linear acid in total acid was 68 mole percent.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A process for preparing carboxylic acids which comprises bringing together in a reaction zone an olefin wherein greater than 50 mole percent of the olefin is an internal olefin, water and carbon monoxide in the presence of a cobalt catalyst and a promoter selected from the group consisting of pyridine, isoquinoline and alkyl pyridines having 1 to 4 carbon atoms in the alkyl chain, the molar ratio of promoter to catalyst being between about 5:1 and 15:1, at pressures from about 70 to about 300 kg/cm², at temperatures above 180° C. and below about 220° C.

2. A process of claim 1 wherein the catalyst is provided by dicobalt octacarbonyl.

3. A process of claim 1 wherein the promoter is pyridine.

4. A process of claim 1 wherein the olefin is a mixture of olefins having 10 to 20 carbon atoms.

5. A process of claim 4 wherein greater than 75 percent of the olefins are internal olefins.

6. A process of claim 4 wherein the olefin is a mixture of olefins having 10 to 14 carbon atoms.

7. A process of claim 1 wherein the temperature is above 180° C. and below about 200° C.

8. A process of claim 1 wherein the molar ratio of pyridine to cobalt is between about 10:1 and 15:1.

9. A process of claim 3 wherein the molar ratio of pyridine to cobalt is between about 8:1 and 12:1.

10. A process of claim 1 wherein the process is carried out in the presence of a saturated carboxylic acid solvent having between 2 and about 20 carbon atoms.

11. A process of claim 6 wherein the process is carried out in the presence of a saturated carboxylic acid solvent having between 11 and 15 carbon atoms.

12. A process of claim 1 wherein the olefin has from 10 to 12 carbon atoms and greater than 75 mole percent of the olefins have unsaturation at other than the terminal position, the promoter is pyridine, the mole ratio of pyridine to cobalt is between about 8:1 and 12:1, and the temperature is above 180° C. and below about 200° C.

13. A process of claim 12 wherein the cobalt catalyst is provided by dicobalt octacarbonyl.

14. A process of claim 1 wherein the cobalt catalyst is provided by a cobalt salt.

* * * * *